Oct. 11, 1949. F. GEHEB Plant Pat. 878
PEACH TREE
Filed Nov. 28, 1947
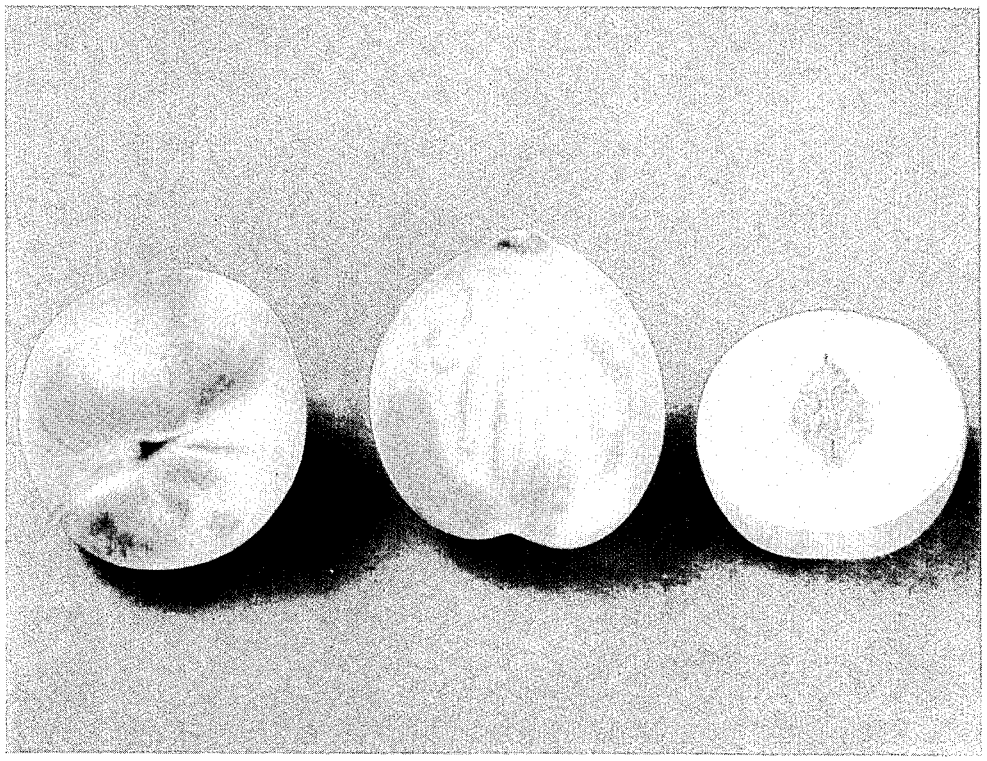
Inventor
Frank Geheb
By Robb & Robb
Attorneys Patented Oct. 11, 1949

Plant Pat. 878

UNITED STATES PATENT OFFICE

878

PEACH TREE

Frank Geheb, Arkadelphia, Ark., assignor to Stark Bro's Nurseries and Orchards Company, Louisiana, Mo., a corporation of Missouri Application November 28, 1947, Serial No. 788,612

1 Claim. (Cl. 47—62)

The present invention relates to a new and distinct variety of peach tree originating as a seedling of the well known "Hal-Berta-Giant" variety (Pl. Pat. #7).

This new variety is characterized as to novelty by the large size of the fruit, the red coloring of the skin and white flesh thereof, and the good eating quality and firmness of the fruit. These characteristics combined with its early ripening season and free stone distinguish this variety from all others now known in commerce. It is, to the best of my knowledge, the earliest ripening white-fleshed, large, free stone peach, maturing ten days before "Red Bird Cling" grown under comparable conditions.

Asexual reproduction of this new variety shows the foregoing characteristics come true to form and are established.

The accompanying drawing illustrates in reduced size, specimens of this new variety from opposite ends and also in section with the stone in place.

The following is a detailed description of the new variety, color terminology being in accordance with the Horticultural Color Guide and Ridgway's Color Standard:

Dates first and last picking: July 4th–July 10th, for 1946 season. Specimens described were asexually reproduced by grafting and grown at Atlas, Illinois.

Tree: Large; vigorous; dense; spreading; vase-formed; hardy; productive.

*Trunk.*—Stocky; medium shaggy.

*Branches.*—Medium stocky; smooth. Color—Chestnut, Plate II, overlaid with Pale Gull Grey, Plate LII, Ridgway's Color Standard. Lenticels—numerous; large.

*Leaves.*—Length—6"; width—1⅜". Large; ovate; acutely pointed; thick; rugose. Color—Parsley Green, Plate 00962, page 193, vol. II, Horticultural Color Guide. Margin—crenate; finely serrate. Petiole—medium length; medium thick. Glands—number—2–7. Opposite on base of leaves; large; reniform; free.

*Flowers.*—Dates first and full blossoms—March 28th–March 30th. Medium early; medium size; pink.

Fruit: Maturity when described—eating; July 8th.

*Size.*—Uniform; large. Axial diameter—3". Transverse in suture plane—2⅞". At right angles to suture plane—2⅞".

*Form.*—Uniform; symmetrical; broadly ovoid; sides unequal.

*Suture.*—Distinct; extends from base to beyond apex; has slight marked depression beyond pistil point.

*Ventral surface.*—Rounded; slightly lipped toward apex; lips, equal.

*Cavity.*—Flaring; elongated on one side. Depth — ½". Breadth — 1". Markings—none.

*Base.*—Truncate; oblique.

*Apex.*—Short; oblique.

*Stem.*—Length, ¼"; stout, glabrous. Adherence to stone—medium.

*Skin.*—Medium thick; tough; free.

*Color.*—Highly blushed red; Blush Currant Red, Plate 821/2, page 167, Horticultural Color Guide. Down — moderate; short; does not roll up when rubbed.

Flesh:

*Color.*—White. Surface of pit cavity—Pod Green, Plate 061/3, page 120, Horticultural Color Guide.

*Juice.*—Moderate; rich.

*Texture.*—Meaty.

*Fibres.*—Few; fine; tender.

*Ripens.*—Fairly even.

*Flavor.*—Subacid.

*Aroma.*—Wanting.

*Eating quality.*—Good.

Stone: Free when fully ripe.

*Fibres.*—Part from flesh smoothly.

*Size.* — Medium. Length — $1\frac{9}{16}$". Thickness—1".

*Form.*—Oval; full.

*Base.*—Oblique. Hilum—narrow, oval.

*Sides.*—Curved on right and left.

*Apex.*—Acute.

*Surface.*—Irregularly furrowed near ventral edge toward apex; pitted from base to above center.

*Ridges.*—Rounded toward apex: pits, elongated; ventral edge, thick with wing from base extending ¾ length of pit.

*Dorsal edge.*—Full with deep groove to above center. Ridges—interrupted.

Use: Market; dessert; canning.

Keeping quality: Medium

Resistance to: Insects—medium. Diseases—good.

Shipping quality: Medium.

I claim:

A new and distinct variety of peach tree characterized as to novelty by the large size of its fruit, its free stone, firm white flesh, deep red-colored skin, good quality and early ripening period, substantially as shown and described.

FRANK GEHEB.

No references cited.